United States Patent [19]

Hazen

[11] Patent Number: 4,749,523
[45] Date of Patent: Jun. 7, 1988

[54] SOLID PHASE ACYLATION OF AMINOSULFONIC ACIDS

[75] Inventor: James R. Hazen, Coventry, R.I.

[73] Assignee: Hoechst Celanese Corporation, Somerville, N.J.

[21] Appl. No.: 725,068

[22] Filed: Apr. 24, 1985

Related U.S. Application Data

[63] Continuation-in-part of Ser. No. 625,941, Jun. 29, 1984, abandoned.

[51] Int. Cl.$^4$ ........................................... C07C 143/53
[52] U.S. Cl. ................................................. 260/507 R
[58] Field of Search ............... 260/507 R, 513 N, 508, 260/509, 510

[56] References Cited

U.S. PATENT DOCUMENTS 4,379,937  4/1983  Corso et al. .................... 260/507 R

FOREIGN PATENT DOCUMENTS 95177  5/1983  European Pat. Off. ........ 260/507 R

OTHER PUBLICATIONS

Chemical Abstracts, vol. 76 Index Guide (1972), pp. 54I–55I and 126I.
Hack's Chemical Dictionary, 4th Edition, McGraw-Hill Book Co., N.Y. 1972, pp. 16 & 86.

Primary Examiner—Nicky Chan
Attorney, Agent, or Firm—Hugh C. Crall

[57] ABSTRACT

This invention is directed to the acylation of aminosulfonic acids in the solid phase. Two discrete, sequential chemical reactions occur, i.e. (1) the neutralization of the aminosulfonic acid, and (2) the subsequent amine acylation, to produce an improved neutralized acyl-aminosulfonic acid at a reduced cost. Aminosulfonic acids having the general formula $HO_3S-A-NH_2$ are acylated to neutralized acyl-aminosulfonic acids having the general formula $RCONH-A-SO_3M$, where A is an unsubstituted or substituted aliphatic, aromatic or heteroaromatic group and M is a neutralizing agent moiety. The yield is virtually quantitative.

4 Claims, No Drawings

SOLID PHASE ACYLATION OF AMINOSULFONIC ACIDS

CROSS REFERENCE TO RELATED APPLICATIONS

This is a continuation-in-part of U.S. patent e application Ser. No. 625,941 filed June 29, 1984, now abandoned.

BACKGROUND OF THE INVENTION

This invention is directed to the acylation of aminosulfonic acids in which the neutralization and acylation of the acid is conducted in the solid phase. Non-gas phase bimolecular reactions generally do not readily occur unless conducted in the condensed phase, e.g. in a solvent or in the molten state. This condition, whether for homogeneous or heterogeneous reactions, is generally essential for the requisite intimate physical and chemical interactions of the reactants. In the present invention, two discrete, sequential chemical reactions occur in the solid phase, i.e. (1) the neutralization step of the sulfonic acid moiety with a base and (2) the subsequent amine acylation, to produce a superior acyl-aminosulfonic acid at a reduced cost. Both essential chemical steps occur virtually quantitatively in the solid phase.

This invention is directed to acylating aminosulfonic acids, in particular the acetylation of aminosulfonic acids with acetic anhydride. The invention has substantial advantages over prior art methods because the prior art involves doing the acylation usually in the homogeneous phase in a solvent, typically water.

There are numerous prior art references to the acetylation of various aminosulfonic acids in water. For example, sulfanilic acid has been acetylated with acetic anhydride in aqueous solution after prior neutralization with potassium carbonate (Berichte, 58, 2286). German patent No. 129,000 also teaches the acetylation of sulfanilic acid and a variety of other phenyl and naphthyl aminosulfonic acids in a similar fashion. A similar industrial process is described in the BIOS Final Report 1149, p. 125 for the manufacture of acetyl sulfanilic acid. Zincke et al (Berichte, 46, 755) and German patent No. 410364 describe the acetylation of metanilic acid with acetic anhydride after neutralization in homogeneous aqueous solution, and Bucherer et al describe the substantially equivalent acetylation of 1-naphthylamino-4-sulfonic acid (J.Prakt Chem. 80, 201). The resulting acetylated materials, however, are generally very soluble in water and isolation requires salting out with substantial quantities of an inorganic salt such as sodium, potassium, or ammonium sulfate or chloride. These procedures result in reduced yield because of solubility losses, and also result in contamination of the product with salts. Other costly methods, such as spray drying, or energy intensive methods, such as evaporating to dryness, have been utilized to separate the product from the aqueous solvent.

Other workers have avoided the problems associated with the aqueous acetylation of aminosulfonic acids by employing a non-aqueous solvent, such as acetic acid or pyridine. German patent Nos.69555, 75084 and 116922 describe acetylations in acetic acid with sodium acetate as base while Kloetzel et al (J.Org. Chem., 26, 607) describe the use of acetic acid as solvent with pyridine as base. A number of works have utilized pyridine as solvent and base for the acetylation of aminosulfonic acids with acetic anhydride (A. Barco et al, Synthesis, 877 (1974); Forster et al, J. Soc.Chem. Indust., 46. 225c, and 47, 156T; Cross et al, J. Soc. Dyers Col., 59, 143 and 147). Even the use of non-aqueous solvents, however, still requires the separation of the bulk of the solvent from the product by filtration.

Some workers have utilized the neutralized, isolated salt, such as an alkali metal or heavy metal salt, of the aminosulfonic acid as the starting material and conducted the acylation, especially acetylation, in excess acetic anhydride (Nietzki et al, Berichte 17, 707; Gnelm et al, J. Prakt. Chem., 63, 405; and Schroefer, Berichte, 39, 1559). However, this has the disadvantage of introducing an additional step in the process, i.e., the isolation of the salt after base neutralization. Furthermore, these publications teach that a solvent, such as water, alcohol, or ether, or combinations of these, are required in the isolation of the acetylated products, again necessitating solvent removal.

The above prior art requires that the solvent-wet product be dried in yet another separate operation. Drying is essential, especially with water-wet products, since wet material is incompatible in the important chemical application of these materials, namely, conversion of the sulfonic acid group to the sulfochloride group with chlorosulfonic acid and/or thionyl chloride or similar reagent.

The present invention eliminates the solvent, salting out, filtration, and drying operation, and thereby substantially increases the process yield at a reduced cost. Importantly, in this age of environmental concern virtually all discharge of waste water or other liquid wastes is eliminated. The present invention directly produces a dry product in high purity and in very nearly quantitative yield. Furthermore, the process described herein is faster, more efficient and has higher space-time yields than prior technology.

SUMMARY OF THE INVENTION

This invention is that of a new process of acylating aminosulfonic acids of the structure:

$HO_3S-A-NH_2$, where A is a substituted or unsubstituted aliphatic, aromatic or heteroaromatic group, to produce the corresponding N-acyl derivatives or sulfonic acid salts thereof as the products of said process. The invention is a method of producing the N-acyl derivatives in the solid, semi-solid, or dough-like state, in the absence of any added solvent or other vehicle to facilitate the reaction. The proces is applicable to aminosulfonic acids and is especially useful in the production of acetylated amino aryl sulfonic acids, a number of which are important dyestuff precursors.

The reaction mass consists only of the reactants, i.e., the starting dry or nearly dry aminosulfonic acid, the acylating agent, and some organic or inorganic compound capable of neutralizing the sulfonic acid moiety, because little or no acylation of the amino group occurs if it is not neutralized. Suitable neutralizing compounds or bases include the alkali or other metal carboxylates, carbonates, hydroxides, alkoxides or similar oxygen bases as well as nitrogeneous bases such as ammonia and amines. Preferred neutralization agents include hydroxides, acetates and carbonates of the alkali and alkaline earth metals. Most preferred are the hydroxides, acetates and carbonates of sodium, potassium, lithium and calcium. The foregoing examples of suitable neutralizing compounds are illustrative and it will be readily apparent to one skilled in the art that there exists a large number of alternative inorganic and organic neutralizing compounds. Examples of acylating agents include the carboxylic acid anhydrides, such as acetic and propionic anhydrides, and other similar reactive acylating agents, such as diketene.

DESCRIPTION OF THE PREFERRED EMBODIMENTS

This invention is that of a process of acylating aminosulfonic acids. An aminosulfonic acid has the general formula, $HO_3S-A-NH_{2'}$, where A is a substituted or unsubstituted aliphatic, aromatic or heteroaromatic group. Typical acids include:
2-Aminobenzenesulfonic acid
3-Aminobenzenesulfonic acid
4-Aminobenzenesulfonic acid
3-Methyl-4-aminobenzenesulfonic acid
2,4-Diaminobenzenesulfonic acid
1-Aminoethanesulfonic acid
1-Amino-4-naphthalenesulfonic acid (Naphthionic Acid)
1-Amino-5-naphthalenesulfonic acid (Laurent's Acid)
1-Amino-8-naphthalenesulfonic acid
2-Amino-1-naphthalenesulfonic acid (Tobias Acid)
2-Amino-5-naphthalenesulfonic acid
2-Amino-6-naphthalenesulfonic acid (Broenner's Acid)
2-Amino-8-naphthalenesulfonic acid (Badische Acid)
8-Amino-1-naphthol-3,6-disulfonic acid (H-Acid)

The moiety A includes alkyl, arylalkyl, substituted and unsubstituted phenyl, naphthyl and heteroaromatic groups which may contain substitutes such as a halogen, hydroxyl, alkyl, alkoxy, sulfo, nitro acylamino or mixtures of such groups. The reaction is conducted by mixing the reactants in equipment having the capability required for the mixing of moist or dry solids or otherwise viscous, heavy, or tacky materials which may pass through a plastic, or dough-like state. Examples of such suitable apparatus are double arm kneader (continuous or batch), ribbon blender, pan dryer, Venuleth, rotary or similar turbulent drying equipment.

The physical state of the reaction mass during the course of the reaction is dependent on the choice of starting materials and reaction time, and can be a more or less free flowing powder, moist solid, or a dough-like mass or a combination of these states. The starting material and a molar excess of base in the range of about 0 to 100% excess, preferably about 5% excess are pre-mixed in the reactor, e.g., a kneader, and then treated in a controlled manner with a molar excess of acylating agent in the range of 0 to 100%, preferably 25–50%, most preferred about 50% excess. The reaction temperature is usually not a critical parameter and the reaction is usually done without external temperature control but such control may be applied where necessary. Depending on the reactants, the reaction may be readily completed in the temperature range from about ambient to about 100° C., preferably from about 30° to about 80° and most preferably from about 30° to about 80° C. The reaction is typically accompanied by a moderate, brief exotherm which peaks at about 40°-50° C. and is rapid, being generally kinetically complete in less than an hour. Typically the reactants will form a dough-like mass during or shortly after the addition of acylating agent which may start to revert back to a solid powder form towards the end of the reaction. The formation of the reaction product's powdery form can be facilitated by removing the volatile material (e.g. water, excess acylating agent, or by-products derived therefrom) from the system by heating the mixture or maintaining it under reduced pressure, or both. The removal of volatile matter is desirable not only to facilitate the discharge of the product in powder form from the reactor but also to free it of odiferous or noxious volatiles or materials, such as water, which are chemically incompatible in certain further chemical processing of the product. Typically, by maintaining the reaction mass under reduced pressure with external heating for one to two hours, the dry acylated product can be recovered in nearly quantitative yield in high purity. Alternatively, the volatile materials may be removed in a stream of air or nitrogen or other suitable gas. The conversion of amine to acylated amine is generally greater than 98%. The following examples are illustrative of the invention.

EXAMPLE 1

Broenners acid (2-naphthylamino-6-sulfonic acid) in an amount of 40 parts is charged into a double-arm kneader with a sigma blade configuration having a capacity of 150 cc, followed by 15 parts of 50% sodium hydroxide with mixing. After mixing for 10–15 minutes, 27 parts of acetic anhydride is added over about five minutes. The reaction mixture forms a soft dough-like mass and the temperature reaches a maximum of about 40°–45° C. within 10–15 minutes. After about 30 minutes the reaction mass is heated externally with steam under reduced pressure to remove water, acetic acid, and excess acetic anhydride. After one to two hours the dry, powdery Acet-Broenners acid sodium salt is discharged from the kneader. The reaction yield is 95 percent and liquid chromatographic analysis indicated a purity of 93% acetylated product which contains a small amount (1.5%) of unconverted Broenners acid.

EXAMPLE 2

Metanilic acid (3-aminobenzenesulfonic acid) in an amount of 37.5 parts, and 18.7 parts of sodium acetate are charged into the kneader and the procedure described and 32 parts of acetic anhydride are added to the reaction mixture. The powdery reaction mass is mixed for one hour and then dried at 85° C. in a stream of air to give a 95% yield of 3-acetylaminobenzenesulfonic acid sodium salt. Liquid chromatography and titration analysis indicated a purity of greater than 97% and the presence of about 0.5% metanilic acid.

EXAMPLE 3

Metanilic Acid in an amount of 37.5 parts and 9.1 parts of sodium hydroxide beads are mixed in a kneader for about 30 minutes and then 32 parts of acetic anhydride are added over a period of 7-8 minutes. During the anhydride addition, the reaction mixture forms a soft dough-like mass. After about one-half hour, the dough-like mass (temperature ca.40° C.) starts to revert to a moist solid. After one hour, external steam heating is applied and the mixture held under vacuum. After 1.5 hours the dry powder is discharged to yield 50.9 parts of white powder, 97.9% pure acet-metanilic acid sodium salt containing 0.1% metanilic acid (96.9% of the theoretical yield).

EXAMPLE 4

H-Acid (8-Amino-1-naphthol-3,6-disulfonic acid), 87.6% as the monosodium salt and containing 10.6% water of hydration, were charged into a kneader in the amount of 60 parts, followed by the addition of 15 parts of sodium acetate. After the solids were mixed for a brief period, 24 parts of acetic anhydride were added gradually with continued mixing. When the addition was complete the reactants were heated by passing steam at a temperature of about 100° C. through the jacket of the kneader for about 1 hr. The kneading mass was then dried by continued heating in a stream of air. The mass was then cooled and the powder discharged from the kneader to give 61 parts of the sodium salt of N-Acetyl-H-Acid (8-acetylamino-1-raphthol-3,6-disulfonic acid) which by liquid chromatography analysis contains about 2.5% of starting H-Acid and about 2.5% of N,O-Diacetyl-H-Acid. This experiment was repeated except the quantity of acetic anhydride was increased from 24 to 35 parts. The amount of starting H-Acid in the product of this experiment was reduced to 0.3%, or less, while the amount of N,O-Diacetyl-H-Acid increased to about 12-14%.

The results from other representative aminosulfonic acids which have been similarly acetylated are presented in Table 1 below.

TABLE 1

Solid Phase Acetylation of Representative Aminosulfonic Acids

| Compound | Base (mole ratio) | Acetic Anhydride (mole ratio) | Yield |
|---|---|---|---|
| Sulfanilic Acid | 50% NaOH, 1.03 | 1.48 | 96.7 |
| 4-Amino-m-toluene sulfonic acid | NaOH, 1.04 | 1.50 | 90.3 |
| Tobias Acid | NaOAc, 1.03 | 1.47 | 95.5 |
| Laurent's Acid | 50% NaOH, 1.05 | 1.47 | 93.8 |
| Badische Acid | NaOH, 1.08 | 1.72 | 96.0 |
| 1,3-Phenylenediamine-4-sulfonic acid | NaOAc, 1.05 | 2.94 | 90.0 |
| 1-Amino-2-ethane sulfonic acid | NaOH, 1.05 | 1.50 | 97.0 |

This method of acylating aminosulfonic acids, in particular with acetic anhydride, has substantial advantages over prior art methods. Prior art technology involves doing the acylation reactions in a solvent, typically water, as a vehicle for the required base neutralization and subsequent acylation. The resulting acylated materials, however, are very soluble in aqueous solvents, requiring the salting out of the product with substantial quantities of inorganic salts such as sodium or ammonium sulfate in order to isolate it by filtration. Such salting out operations inevitably result in loss of yield via solubility losses and contamination of the product with salts.

Furthermore, certain acylated aminosulfonic acids are so water soluble that they cannot readily be salted out with inorganic salts and are inconvenient and difficult to isolate. In cases such as these, as for example with 1-acetamino-5-naphthalene sulfonic acid and 2-acetamino-5-naphthalenesulfonic acid, the product can only be precipitated from aqueous solution by acidifying to below pH 1 with a strong mineral acid such as hydrochloric acid. This particular technique is undesirable relative to the present invention for two additional reasons. The first is that such products present special safety and handling difficulties due to the fact that they are highly acidic. The second is that such acidic materials present special difficulties during drying due to the corrosive nature of the mineral acids and their vapors. Such drying requires specialized corrosion-resistant drying equipment. The solid phase technique is uniquely advantageous not only in its simplicity of operation but also by its universality of application to virtually all aminosulfonic acids regardless of variations in chemical structure, water solubility, and other physical and chemical properties.

Yet another and unanticipated advantage of the solid phase method relative to the aqueous methods is found in those products which are isolated from aqueous solutions by salting out with ammonium sulfate. Two examples of such products isolated as their ammonium salts are 2-acetamino-6-naphthalenesulfonic acid and 2-acetamino-8-naphthalene sulfonic acid. It has been found, however, that these products prepared via the solid phase method as their sodium salts give distinctly higher yields than the corresponding ammonium salts in their subsequent conversion to the corresponding sulfonyl chlorides. In particular, the 2-acetamino-6-naphthalenesulfonic acid via the solid phase technique is converted to the sulfochloride consistently in 8-9% higher yield (95% vs. 86% of theory) than the product via the aqueous ammonium sulfate salting out technique. Similar results are obtained with the conversions of 2-acetamino-8-naphthalenesulfonic acid salts to the sulfochloride. These results are demonstrably due to the yield-lowering effect of the ammonium ion versus the sodium ion in the chlorosulfonation. Thus, in addition to the advantages previously cited, the solid phase technique has the additional and unexpected advantage of allowing certain products which were previously best isolated from water as their ammonium salts to now be optimally isolated as their sodium salts and thereby allow higher yields in their subsequent conversion to the sulfochlorides. The solid phase reaction thus allows one to use whichever neutralizing agent (base) he desires without taking into consideration subsequent processing parameters of the neutralized acyl-aminosulfonic acid. The increased yield afforded in the subsequent processing steps can be significant in these relatively high cost chemicals.

Previously other cumbersome methods such as spray drying for separating the product from the solvent have been utilized. Even the use of non-aqueous solvents, such as acetic acid, still entails the necessity of separating the product from the bulk of the solvent vehicle by filtration. These prior art technologies, moreover, still require that the isolated solvent-wet products be dried in a separate operation. Drying is essential, particularly with water-wet products, since wet material is incompatible in most chemical applications of these products, namely the conversion of the sulfonic acid to its sulfochloride with chlorosulfonic acid and/or thionyl chloride.

The present invention, by eliminating the solvent, eliminates the salting out, filtration and subsequent drying steps, and thereby also eliminates yield losses and, importantly, virtually all discharge of waste water. Not only are large waste water discharges eliminated, but also the solid phase technique readily allows the recovery of the volatile organic by-product from the acylation by simple methods. For example, in the case of acetic anhydride as the acylating agent, the valuable by-product acetic acid can be recovered and reclaimed nearly quantitatively simply by condensing its vapors during the drying operation. Such a recovery is not feasible in aqueous acetylations (or other acylations), and all the by-product acetic acid must be discarded in the waste water. The present invention directly produces a dry product in high purity and in nearly quantitative yield. Furthermore, the process described herein is faster and has higher space-time yields than the existing technology, and provides a very simple and general method which is universally applicable to all aminosulfonic acids and gives products in the most suitable physical and chemical form for subsequent chemical conversions.

I claim:

1. A process for producing a neutralized acyl- aminosulfonic acid comprising:
   (1) contacting an aminosulfonic acid of the general formula; $H_2N-A-SO_3H$ with a neutralizing agent, where A is a moiety selected from the group consisting of substituted or unsubstituted aliphatic and aromatic groups;
   (2) mixing said neutralizing agent and said aminosulfonic acid in the solid phase to effect neutralization of said acid;
   (3) contacting said neutralized aminosulfonic acid with a carboxylic anhydride acylating agent under agitation in the solid phase and
   (4) maintaining the solid phase reaction mass of neutralized aminosulfonic acid and acylating agent under agitation to effect acylation of the amino group of said aminosulfonic acid salt.

2. A process according to claim 1 wherein A is selected from the group consisting substituted or unsubstituted alkyl, arylalkyl, phenyl, naphthyl and heteroaromatic.

3. The process according to claim 1 wherein said neutralizing agent is selected from the group consisting of metal carboxylates, carbonates, hydroxides, alkoxides, and oxides of sodium, lithium, potassium and calcium.

4. The process according to claim 3 wherein said moiety A is selected from the group consisting of substituted or unsubstituted phenyl and naphthyl.

* * * * *

UNITED STATES PATENT AND TRADEMARK OFFICE
CERTIFICATE OF CORRECTION

PATENT NO. : 4,749,523
DATED : June 7, 1988
INVENTOR(S) : James R. Hazen

It is certified that error appears in the above-identified patent and that said Letters Patent is hereby corrected as shown below:

Please correct the following typographical errors for the above-identified U.S. Patent:

Column 1, line 8, please delete -- e -- after the word "patent".

Column 2, line 53, please correct the word "proces" to read as -- process --.

Column 2, line 65, the word "nitrogeneous" should read as -- nitrogenous --.

Column 4, line 45 - 46, after the word "kneader", please delete -- and the procedure described --.

Column 5, line 16 - 17, the phrase "(8-acetylamino-1-raphthol-3,6-disulfonic acid)" should read as -- (8-acetyl-amino-1-naphthol-3,6-disulfonic acid) --.

Column 6, line 16, the phrase "acetamino-8-naphthalene sulfonic acid" should read as -- acetamino-8-naphthalenesulfonic acid --.

Signed and Sealed this

Thirty-first Day of January, 1989

Attest:

DONALD J. QUIGG

Attesting Officer      Commissioner of Patents and Trademarks